(12) United States Patent
Arun et al.

(10) Patent No.: US 9,687,364 B2
(45) Date of Patent: Jun. 27, 2017

(54) INJECTION MOULDABLE POLYMERIC COMPOSITE BASED PASSIVE POLYCENTRIC KNEE JOINT

(71) Applicants: DEPARTMENT OF BIOTECHNOLOGY, MINISTRY OF SCIENCE & TECHNOLOGY, New Delhi (IN); Indian Institute of Technology Guwahati, Assam (IN)

(72) Inventors: Srinivasan Arun, Assam (IN); Subramani Kanagaraj, Assam (IN)

(73) Assignees: DEPARTMENT OF BIOTECHNOLOGY, MINISTRY OF SCIENCE & TECHNOLOGY, New Delhi (IN); INDIAN INSTITUTE OF TECHNOLOGY GUWAHATI, Assam (IN)

( * ) Notice: Subject to any disclaimer, the term of this patent is extended or adjusted under 35 U.S.C. 154(b) by 1 day.

(21) Appl. No.: 14/840,052

(22) Filed: Aug. 31, 2015

(65) Prior Publication Data
US 2016/0089243 A1 Mar. 31, 2016

(30) Foreign Application Priority Data
Sep. 25, 2014 (IN) .......................... 2761/DEL/2014

(51) Int. Cl.
*A61F 2/64* (2006.01)

(52) U.S. Cl.
CPC ...... *A61F 2/644* (2013.01); *A61F 2210/0076* (2013.01)

(58) Field of Classification Search
CPC ..... A61F 2/64; A61F 2/644; A61F 2210/0076
See application file for complete search history.

(56) References Cited

U.S. PATENT DOCUMENTS

| 708,685 A * | 9/1902 | White ..................... A61F 2/602 623/26 |
| 4,310,932 A * | 1/1982 | Nader ..................... A61F 2/644 623/39 |

(Continued)

*Primary Examiner* — Bruce E Snow
(74) *Attorney, Agent, or Firm* — Mark M. Friedman

(57) ABSTRACT

The present invention mainly relates to knee joint and more particularly to the polymeric composite or nanocomposites based polycentric knee joint. In one embodiment the knee joint comprising: a top part having a top face and a bottom face, wherein the top face having an adapter coupled firmly with the top part to transfer the load from the stump of amputee via socket, a bottom part having a top face and a bottom face, at least one middle linkage pivotably coupling a middle posterior region of the top part with a middle posterior region of the bottom part, at least two side identical linkage pivotably coupling a sides of the top part with a sides of the bottom part, a compression spring along with cylindrical rod positioned in the interior of the bottom part which provides the engaging and disengaging of the top and bottom part, at least two extension spring couples the top and bottom part through two tiny holes and through simple supported beam in the top and bottom part for the flexion and extension of the knee joint and a bumper positioned in the base of the bottom part which contacts with the pylon to absorb the vibration and the terminal impact during the hip hike.

12 Claims, 2 Drawing Sheets

(56) References Cited

U.S. PATENT DOCUMENTS

| | | | |
|---|---|---|---|
| 4,911,709 A * | 3/1990 | Marlow | A61F 2/644 |
| | | | 623/39 |
| 6,086,616 A * | 7/2000 | Okuda | A61F 2/644 |
| | | | 623/44 |
| 2003/0153853 A1* | 8/2003 | Houser | A61F 5/0123 |
| | | | 602/16 |
| 2011/0022185 A1* | 1/2011 | Cheng | A61F 2/642 |
| | | | 623/44 |
| 2014/0277581 A1* | 9/2014 | Steele | A61F 2/68 |
| | | | 623/24 |

* cited by examiner

INJECTION MOULDABLE POLYMERIC COMPOSITE BASED PASSIVE POLYCENTRIC KNEE JOINT

FIELD OF THE INVENTION

The present invention mainly relates to knee joint and more particularly to the polymeric composite or nanocomposites based polycentric knee joint.

BACKGROUND OF THE INVENTION

A knee joint is well known in the art which is one of the strongest and most important joints in the human body. It allows the lower leg to move relative to the thigh while supporting the body's weight. Movements at the knee joint are essential to many everyday activities, including walking, running, sitting and standing.

The issues due to osteoarthritis and other knee diseases such as rheumatoid arthritis, psoriatic arthritis, etc's are solved by knee replacement which is a surgical procedure to replace the weight-bearing surfaces of the knee joint to relieve pain and disability.

In major issues, the artificial prosthetic knee joint imitates the functions of the human knee. Prosthetic knee joints use various techniques to allow the leg to be bent and to allow the lower leg to be swung forward after the bending movement. In knee joints, the knee joint angle (angle between the thigh and the shank) is one of the important parameters for determining the proper functioning of the knee.

The existing artificial prosthetic knee joint is classified into two types: single axis and multi axes knee joint. In a single axis knee joint, which is also called as a fixed knee, the locking mechanism is controlled by the amputee. In this design, knee stability during weight-bearing is achieved by positioning the knee axis in such a way, relative to the body-weight action line, that the knee can be extended. In addition, a movement from active hip-extension muscles is required during the weight-bearing phase of the walking cycle. This means that the amputee must walk during weight-bearing over a fully extended knee, which is physiologically abnormal and contributes to the unnatural appearing gait of the "above-knee" amputees.

In case of multi axes knee joint, the locking of the knee is controlled by self weight of the patient, which also acts as a brake to prevent the bending of the knee. The multi axes knee joint is composed of multi-links mostly four-bar link used for knee mechanism which has better functionality when compared to a single-axis knee joint, which is also called as a polycentric knee joint.

In addition, these knee joints generally have been complicated in structure, including complex spring and/or hydraulic mechanisms to achieve the desired performance, which has resulted in high cost, heavy weight, and inadequate reliability.

Moreover, still now there is no low cost passive polycentric knee joint with superior functionality. The gait analysis along with constrains of ICR, optimum link length, flexion angle, transmission angle and voluntary control zone are not well defined. Further, the existing knee joints are found to be heavy weight and expensive due to the presence of actuators in the active knee joint and there are many amputees, who are not able to afford the knee joint from under developed and developing countries. The extension bias in the passive polymer knee joint is not achieved fully to take care of the buckling of the knee joint during swing phase.

Many trails with resilience device springs came into picture in passive knee joint to achieve the extension bias. But, the normal walking gait cycle is still a concern. In addition to this, controlling of different phases such as stance phase and swing phase is still a major concern in knee joint.

Therefore there is a need in the art with the polymeric composite or nanocomposites based passive polycentric knee joint to solve the above mentioned limitations with affordable price.

OBJECTIVE OF THE INVENTION

The main objective of the present invention is to develop an injection mouldable, cost effective, polymeric composite or nanocomposites based passive polycentric knee joint with extension bias.

SUMMARY OF THE INVENTION

An aspect of the present invention is to address at least the above-mentioned problems and/or disadvantages and to provide at least the advantages described below.

Accordingly, in one aspect of the present relates to a polymeric composite or nanocomposites based passive polycentric knee joint, the knee joint comprising: a top part having a top face and a bottom face, wherein the top face having an adapter coupled firmly with the top part to transfer the load from the stump of amputee via socket, a bottom part having a top face and a bottom face, at least one middle linkage pivotably coupling a middle posterior region of the top part with a middle posterior region of the bottom part, at least two side identical linkage pivotably coupling a sides of the top part with a sides of the bottom part, a compression spring along with cylindrical rod positioned in the interior of the bottom part which provides the engaging and disengaging of the top and bottom part, at least two extension spring couples the top and bottom part through two tiny holes and through supported beam in the top and bottom part for the flexion and extension of the knee joint and a bumper positioned in the base of the bottom part which contacts with the pylon to absorb the vibration and the terminal impact during the hip hike.

Other aspects, advantages, and salient features of the invention will become apparent to those skilled in the art from the following detailed description, which, taken in conjunction with the annexed drawings, discloses exemplary embodiments of the invention.

BRIEF DESCRIPTION OF THE DRAWINGS

The above and other aspects, features, and advantages of certain exemplary embodiments of the present invention will be more apparent from the following description taken in conjunction with the accompanying drawings in which:

FIG. 5 shows the top part of polycentric knee joint according to one embodiment of the present invention.

FIG. 6 shows the bottom part of polycentric knee joint according to one embodiment of the present invention.

FIG. 7 shows the fixation of extension assist by means of overhanging beam or cantilever beam according to one embodiment of the present invention.

Figure 1:
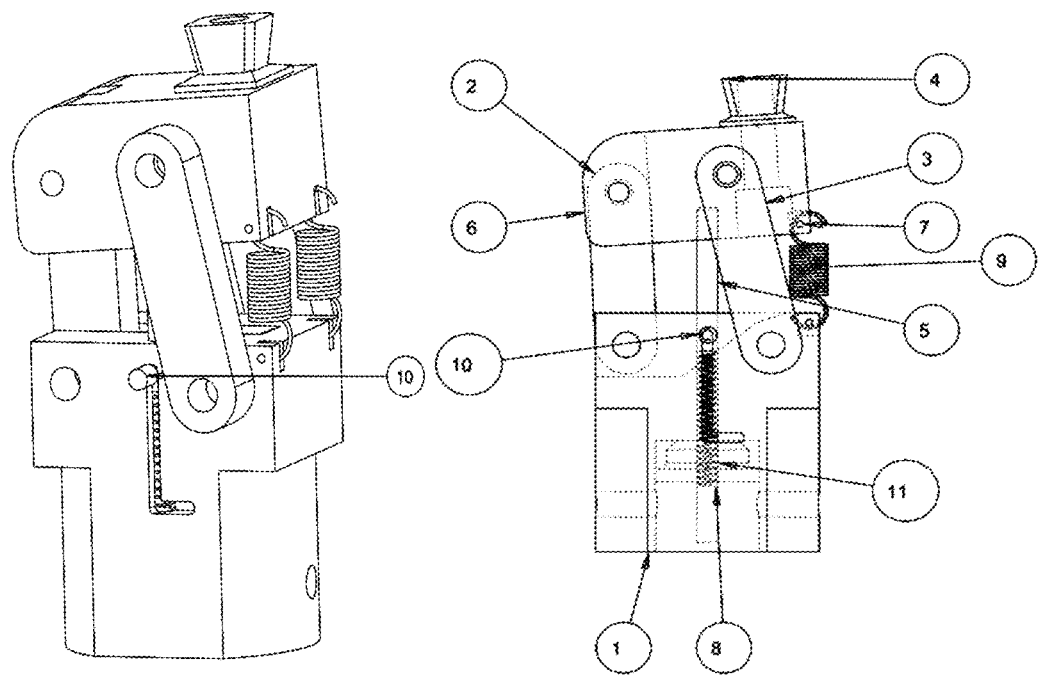
FIG. 1 shows the assembly of polycentric knee joint along with different functional components under locking condition according to one embodiment of the present invention.

Persons skilled in the art will appreciate that elements in the figures are illustrated for simplicity and clarity and may have not been drawn to scale. For example, the dimensions of some of the elements in the figure may be exaggerated relative to other elements to help to improve understanding of various exemplary embodiments of the present disclosure.

Throughout the drawings, it should be noted that like reference numbers are used to depict the same or similar elements, features, and structures.

DETAIL DESCRIPTION OF THE INVENTION

The following description with reference to the accompanying drawings is provided to assist in a comprehensive understanding of exemplary embodiments of the invention as defined by the claims and their equivalents. It includes various specific details to assist in that understanding but these are to be regarded as merely exemplary. Accordingly, those of ordinary skill in the art will recognize that various changes and modifications of the embodiments described herein can be made without departing from the scope and spirit of the invention. In addition, descriptions of well-known functions and constructions are omitted for clarity and conciseness.

The terms and words used in the following description and claims are not limited to the bibliographical meanings, but, are merely used by the inventor to enable a clear and consistent understanding of the invention. Accordingly, it should be apparent to those skilled in the art that the following description of exemplary embodiments of the present invention are provided for illustration purpose only and not for the purpose of limiting the invention as defined by the appended claims and their equivalents.

It is to be understood that the singular forms "a," "an," and "the" include plural referents unless the context clearly dictates otherwise. Thus, for example, reference to "a component surface" includes reference to one or more of such surfaces.

By the term "substantially" it is meant that the recited characteristic, parameter, or value need not be achieved exactly, but that deviations or variations, including for example, tolerances, measurement error, measurement accuracy limitations and other factors known to those of skill in the art, may occur in amounts that do not preclude the effect the characteristic was intended to provide.

FIGS. 1 through 7, discussed below, and the various embodiments used to describe the principles of the present disclosure in this patent document are by way of illustration only and should not be construed in any way that would limit the scope of the disclosure. Those skilled in the art will understand that the principles of the present disclosure may be implemented in any suitably arranged communications system. The terms used to describe various embodiments are exemplary. It should be understood that these are provided to merely aid the understanding of the description, and that their use and definitions, in no way limit the scope of the invention. Terms first, second, and the like are used to differentiate between objects having the same terminology and are in no way intended to represent a chronological order, unless where explicitly stated otherwise. A set is defined as a non-empty set including at least one element.

The present invention is for developing light weight, durable and user friendly artificial limbs through Nanotechnology-based modification of conventional materials and optimizing mechanical component design for enhancing their functional performance. The present invention prosthetic knee joint is made of polymer composites or nanocomposites, and the life span of the same is expected to be increased by adding suitable additives and reinforcements by reducing the environmental degradation by shelf-ageing. The extension bias is also achieved with the spring assisted system using a simply supported beam. Hence, a light weight-passive-prosthetic knee joint made of polymer composites or nanocomposites is developed along with spring assisted extension bias. The development of artificial leg (prosthetic knee joint) at low cost along with reduced weight has been increasing due to advancement of the materials and technology used in the prosthesis. Further, there are many polymeric knee joints developed with the extension bias, which is achieved by the elastic cable during the swing phase with less durability.

The present invention injection mouldable polymeric composite or nanocomposites based passive polycentric knee joint is designed with required considerations such as Grashof criterion, transmission angle, flexion angle constraints and voluntary control zone. The link assembly of the knee joint is made of rigid polymer composites or nanocomposites, which provide the required relative motion, compact, cost effective and negligible degradation with time. The extension bias is made using two parallel extension springs in the symmetric manner using a simply supported beam in top and bottom part of the knee joint, where the stability of the joint during the flexion-extension motion, swing and stance phase is maintained. In order to convert the polycentric knee joint into a single axis knee joint, it is locked by a link along with a groove, as a stopper in the top part 6. The extension springs aid to bring the knee joint back to original position after flexion. Because of the inherent self lubricating characteristics of the polymer, wear occurred between the top and bottom part of the knee joint is taken care in order to avoid the buckling. Thus, the design of cost effective polymeric composite or nanocomposites based passive polycentric knee joint is designed and made with required stability.

FIG. 1 shows the assembly of polycentric knee joint along with different functional components under locking condition according to one embodiment of the present invention.

The figure shows the assembled view of the polymeric composite or nanocomposites based polycentric knee joint under locking condition, where the part 10 is in its extreme position to avoid the buckling of the knee joint when used in uneven surfaces. The polycentric knee joint has top part 6, bottom part 1, at least middle linkage/another link 2, at least two side identical linkages/two identical links 3, compression spring 8, at least two extension springs 9, bumper 11, holder 10, adapter 4, cylindrical rod 5, and supporting beams 7, etc. The top part 6 includes a top face and a bottom face, where the top face includes an adapter 4 which is coupled firmly with the top part 6 to transfer the load from the stump of amputee via socket. The bottom part 1 includes a top face and a bottom face. The bottom face of the top part 6 and the top face of the bottom part 1 are flat and each comprises low friction surfaces. Further, the bottom face of the top part and the top face of the bottom part consists of two tiny holes which receives the extension spring through supporting beam which allows for the flexion and extension bias of the knee joint. The bottom part 1 of polycentric knee joint further includes a holder 10 in top face of bottom part 1 which has a knurling surface for easy gripping to achieve the locking mechanism safely.

The middle linkage/another link 2 of the polycentric knee joint pivotably couples an internal middle posterior region of the top part 6 with an internal middle posterior region of the bottom part 1. The middle linkage/another link 2 comprises a bar having a first end and a second end, the first end being pivotably coupled to the middle posterior region of the top part 6 and the second end being pivotably coupled to the middle posterior region of the bottom part 1.

The polycentric knee joint includes at least two side identical linkage/two identical links 3 comprises a bar having first end and a second end which pivotably coupling the sides of the top part 6 with the sides of the bottom part 1. The side linkage 3 comprises of first side linkage (3(1)) and a second side linkage (3(2)). The first side linkage is disposed on a first side of the top part 6 and on a first side of the bottom part 1, and where the second side linkage is disposed on a second side of the top part 6 and on a second side of the bottom part 1. Further the side linkages/identical links 3 are disposed externally to the sides of the top part 6 and the sides of the bottom part 1.

The compression spring 8 along with cylindrical rod 5 positioned in the interior of the bottom part 1 which provides the engaging and disengaging of the top and bottom part 1. The engagement of the cylindrical rod 5 is carried out with the compression spring 8 and the holder 10 using the slot provided, which makes the movements in the four bar mechanism were arrested when the knee joint is used in the uneven surfaces like steps and hilly region. The disengagement of the cylindrical rod 5 is carried out with the compression spring 8 and the holder 10 using the slot provided, which allows the four bar mechanism to activate in order to perform the walking motion. The polycentric knee joint further includes at least two extension springs 9 which couples the top and bottom part 1 through two tiny holes and a supported beam 7 in the top 6 and bottom part 1 for the flexion and extension of the knee joint.

The bumper 11 positioned in the base of the bottom part 1 which contacts with the pylon to absorb the vibration and the terminal impact during the hip hike. Further, the bumper 11 is specially designed to provide cushioning effect using a step for the prosthetic knee joint. The adapter 4 of top part 6 is made up of rigid material which is clamped with top part 6 to connect the socket with top part 6.

The polycentric knee joint includes a cylindrical rod 5 which is made to function through a hole for engaging and disengaging the top 6 and bottom part 1 which is coupled to holder 10 using threaded joint.

Figure 2:
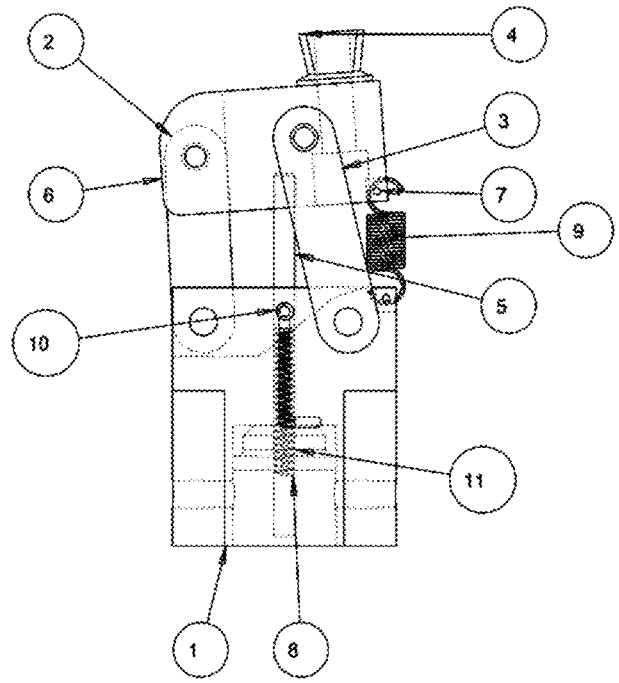
FIG. 2 shows the front view of the polycentric knee joint in locking condition according to one embodiment of the present invention.

FIG. 2 shows the front view of the polycentric knee joint in locking condition according to one embodiment of the present invention.

The figure shows the front view of the polycentric knee joint in locking condition. The figure shows the different parts of the polycentric knee joint by numbering. The polycentric knee joint has top part 6, bottom part 1, at least middle linkage/another link 2, at least two side identical linkages/two identical links 3, compression spring 8, at least two extension springs 9, bumper 11, holder 10, adapter 4, cylindrical rod 5, and supporting beams 7, etc.

The bottom part 1 is connected with the pylon where the respective provision for inserting and locking the pylon was made. The bumper 11 is kept with base of the bottom part 1, which contacts with the pylon to absorb the vibration and the terminal impact during the hip hike. The bumper 11 is specially designed to provide cushioning effect using a step for the prosthetic knee joint. The adapter 4 is connected firmly with the top part 6 to transfer the load from the stump of amputee via socket. An additional projection on adapter 4 is made in order to avoid its rotation in part 6, where a special groove is made for the same. The adapter 4 is designed to distribute the weight of the amputee evenly on the top part 6. The two identical links/side linkages 3 and another link/middle linkage 2 were connected with the top 6 and bottom part 1 of the knee joint to obtain the relative motion between 6 and 1. The connection of link 3 on top part 6 assured the initiation of the swing phase with the inclination in the top part 6. The polymer links (identical links/side linkages and another link/middle linkage) 3 and 2 were curved on their edges to avoid the accidents to be happened due to sharp edges. The locking mechanism between top and bottom part consists of a cylindrical rod, compression spring and a holder. The cylindrical rod 5 was made to function through a hole for engaging and disengaging the top and bottom part. A holder 10 has a knurling surface for easy gripping to achieve the locking mechanism safely, whenever it is needed by the amputee. The holder 10 is connected with the cylindrical rod 5 using threaded joint. The cylindrical rod 5 compressed the spring 8 with the help of a holder while disengaging the locking mechanism.

Further the figure shows the engagement or locking of the knee mechanism, i.e. the movements in the four bar mechanism were arrested when the knee joint is used in the uneven surfaces like steps and hilly region. The disengagement of the cylindrical rod 5 was carried out with the compression spring 8 and the holder 10 using the slot provided, which allows the four bar mechanism to activate in order to perform the walking motion.

Figure 3:
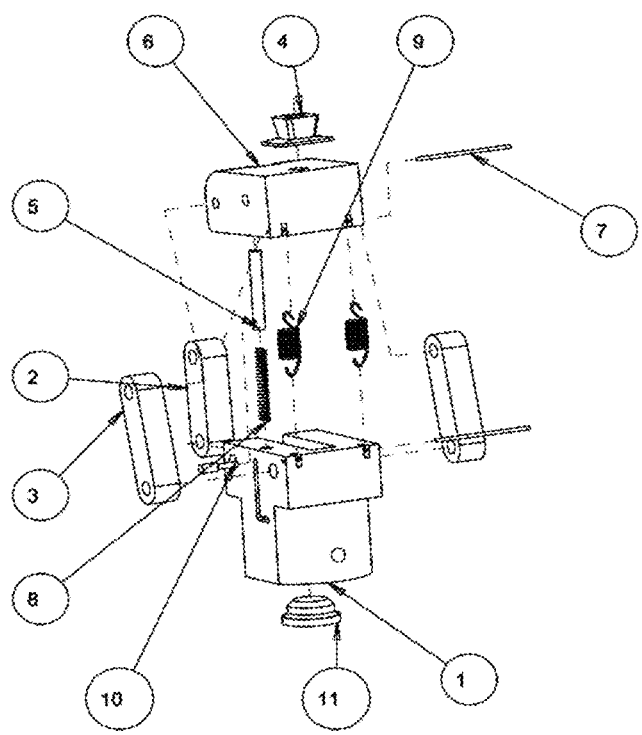
FIG. 3 shows the exploded view of the polycentric knee joint assembly according to one embodiment of the present invention.

FIG. 3 shows the exploded view of the polycentric knee joint assembly according to one embodiment of the present invention.

The figure shows the exploded view of various parts of polycentric knee joint assembly along with corresponding axis for their assembly. The assembly of the compression spring 8 along with their components for engagement and disengagement is shown clearly. The swing phase is initiated by the hip moment given by the amputee, where the extension bias after the flexion is carried out by the two parallel extension springs 9 connected with the top part 6 and bottom part 1 using two simply supported beams 7. The simply supported beams were tightly fit with the top part 6 and bottom part 1 in such a way that the extension spring 9 is also assembled tightly. The hook in the extension springs 9 is rigid to hold the simply supported beams 7. The extension springs 9 bring back the flexed part to the original position and act as bias for the extension.

Figure 4:
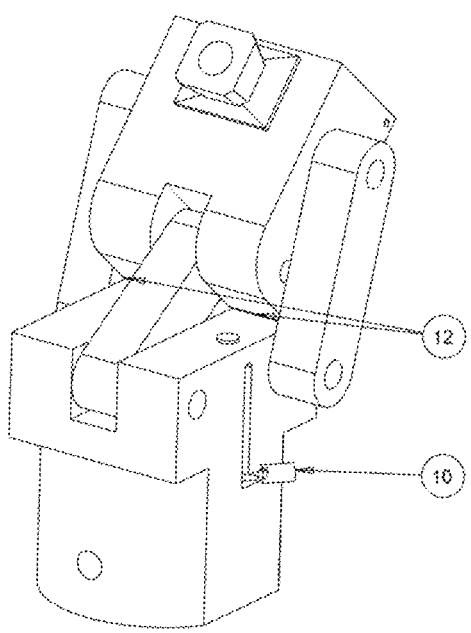
FIG. 4 shows the bearing surface of top and bottom part of the polycentric knee joint assembly along with disengaged locking mechanism according to one embodiment of the present invention.

FIG. 4 shows the bearing surface of top and bottom part of the polycentric knee joint assembly along with disengaged locking mechanism according to one embodiment of the present invention.

The figure shows the bearing surface of top 6 and bottom part 1 of the polycentric knee joint assembly along with disengaged locking mechanism. Further, the figure also shows the articulating section 12 between the top part 6 and bottom part 1 to avoid the buckling, when the prosthetic knee joint is in swing phase.

FIG. 5 shows the top part of polycentric knee joint according to one embodiment of the present invention.

The figure shows the top part 6 of polycentric knee joint. The top part 6 has some features and it is shown figure, which connects the knee joint with the socket. The hole 6A is made for the connection of adapter 4 with top part 6, which has a counter boring to facilitate the fixation of the adapter firmly using the allen bolt. 6B accounts for the two tiny slots in the top part 6, where holding of the extension spring 9 takes place using the simply supported beam 7. The tiny slot gives the advantage of fixing the simply supported beam firmly during the flexion and extension of the knee joint. 6C fixes the top part 6 and the link 3, which plays a role for the initiation of the swing phase for knee mechanism. 6D corresponds to a hole, where a rod, which acts as a simply supported beam, is tightly fixed. 6E is the stopper, which restricts the flexion of the knee joint while sitting. 6F corresponds to the curved surface that accounts for the free movement of knee mechanism. 6G connects the link 2 (additional/middle linkage) with the top part 6. 6H is made to take care of the articulation with the bottom part 1 in order to avoid buckling during the swing phase.

FIG. 6 shows the bottom part of polycentric knee joint according to one embodiment of the present invention.

The figure shows the bottom part of polycentric knee joint. The bottom part of polycentric knee joint includes two tiny slots 1A for the fixation of extension spring 9 using the simply supported beam 7 inserted through a hole 1C. The tiny hole fixes the extension spring 9 rigidly during the swing phase. 1B is made on the bottom part 1 to activate the free movement of prosthetic knee mechanism by the link 2. 1D corresponds to the connection of the link 3 (first and second side linkage) with bottom part 1 in order to get the relative motion. 1E is used to fix the pylon rigidly with the knee joint, where a hole is made on the pylon for the connection. 1F gives provision for resting the holder 10, and it accounts for the easy accessibility of the holder by the amputee during disengaging. 1G is the surface where articulation between top and bottom part occurs and the contact between them helps to prevent the buckling of the knee joint. During sitting position, the wear is expected to occur when the friction between two parts is exceeded. 1H helps to move the link 2 freely during the flexion motion and it also assists the relative motion between link 2 and the bottom part 1. 1I is the provision given for locking mechanism, when the spring, cylindrical rod and the holder were assembled together. 1J helps to provide connection between the link 2 and the bottom 1 and paves a way for the relative motion between them, when the flexion of knee joint takes place. 1K provides the path for the holder while engaging and disengaging the cylindrical rod for restricting the knee mechanism. It also acts as a stopper for the holder, when the polycentric knee joint is converted in to a single axis knee joint.

FIG. 7 shows the fixation of the extension assist using overhanging or cantilever beam according to one embodiment of the present invention.

The figure show the fixation of extension assist using overhanging or cantilever, where the beam was extended in the overhanging or cantilever pattern to hold the extension spring. The beam 7 was extended outwards and the cylindrical block 7A was used to firmly attach the extension assist between top and bottom part. The extension of the beam should be as minimum as possible to avoid the bending of the beam for the efficient function of the knee joint during swing phase. The overhanging beam or cantilever beam is used to firmly attach the extension assist between top and bottom part of the knee joint.

The prosthetic knee joint is one of the complex parts for the trans-femoral amputee to replicate the human walking cycle. It is also reported that nearly 1.7 million people in US have been living with limb loss. Out of the total amputation, Upper extremity amputee (UEA) and lower extremity amputee (LEA) constitute 13 and 87%, respectively.

Generally, the prosthetic knee joint mainly classified into two types: single axis and multi axes knee joint. In a single axis knee joint, which is also called as a fixed knee, the locking mechanism is controlled by the amputee. In case of multi axes knee joint, the locking of the knee is controlled by self weight of the patient, which also acts as a brake to prevent the bending of the knee. The multi axes knee joint is composed of multi-links mostly four-bar link used for knee mechanism, which is also called as a polycentric knee joint. The knee joint angle (angle between the thigh and the shank) is one of the important parameters for determining the proper functioning of the knee. It is known that the instantaneous centre of rotation (ICR) of the polycentric knee joint varied throughout the normal walking of the amputee, which inherently led to improve the stability of the knee joint. The initiation of the knee movement was described by the muscular hip moment exerted by the stump. The load line, ICR, ground reaction force (GRF) and the braking moment generated by the knee helped for the proper functioning of the knee joint. The hip extension moment gives the forward floor reaction and the hip flexion moment gives the backward floor reaction by varying the load line.

A common region called zone of voluntary stability was defined, where ICR falls on the zone for the stability of the mechanism during the heel-contact and push-off of the amputee. The required hip moment for initiating the swing phase and to maintain the stability during the stance phase was derived from the mechanism constraints. The large hip flexion moment and the extension moment led to large zone of voluntary stability. The reduced voluntary control zone led to the higher location (above the knee) of the ICR to maintain the knee stability. The ICR of the knee joint is located above the usual knee joint and within the zone of voluntary stability. The kinematics of the knee joint along with ICR of the four-bar so mechanism, where they evaluated the required hip moment and the minimum energy required to initiate the knee mechanism.

The effective use of GRF achieves the stability of the knee joint. The necessity of the gap between feet and ground was also evaluated to avoid the collision. It was observed that many patients tilt their body to support leg side or draw an arc in horizontal plane during the swing phase. It was also observed that the effective crus (the distal part of the stump) length in the prosthesis is shortened due to the variation of the ICR while bending the knee joint.

The force and torque analysis of the knee joint in the primary ICR axis was introduced. The driving knee and hip joint moment were studied and the axis on the shank was confirmed to be suitable for the control axis.

The knee joints are classified into three types based on the actuation of the knee mechanism: passive mechanical knee joint, semi-active knee joint and active knee joint.

A non-fluid based passive knee joint using friction and spring system was designed. It was confirmed that an additional spring in the extension bias led to increase the walking speed, decrease the heel rise and the duration of swing phase. It was also confirmed that the addition of friction in knee reduced the heel rise and the terminal impact, which was further reduced by the implementation of extension bumper.

A semi-active knee joint using a closed-loop position servo control system for powered prosthesis in human leg was developed. The gait parameters of the young healthiest person were compared with the gait parameters of the newly developed human leg, where a close resemblance between them was observed.

A magneto rheological (MR) damper based prosthetic knee joint was introduced, which showed good performance only in the swing phase.

Later, a prototype of semi-active knee joint was developed. The biomechanical parameters such as stance duration, knee flexion angle and hip flexion angle were studied at different cadence (rhythm of person's walk) such as 88, 96 and 104 step/min. It was observed that there was no significant difference in parameters for the different cadences.

The passive prosthetic knee joint can be used only by the amputee having sufficient stump length. However, the passive knee joint was not utilized fully because of the extensive availability of semi-active and active knee joint. It showed that the passive knee joint was not developed fully to satisfy the amputee. The high end prosthetic knee joint was very difficult to afford by the amputee from under developed and developing countries. Though, the light weight prosthetic knee joint with polymer was also developed, the extension bias and bumper to take care of the terminal impact were not implemented. Later, the extension bias for the polymer knee joint was developed using a cable. But, the durability of the extension cable was not achieved. In addition to the usage of polymer for making the polycentric knee joint has another problem of its degradation with time and the life time of the knee joint decreased compared to the conventional metallic knee joint.

Novel Features of the Invention:

The present invention prosthetic knee joint is made by the assembly of top part, bottom part, small link and large link, which were manufactured by the injection mouldable polymer composites or nanocomposites.

The present invention prosthetic knee joint energy recovered by the polymer composites or nanocomposites used by the knee joint absorbs and releases the energy whenever it is required.

The present invention prosthetic knee joint top part including the curved surface for wear resistant which is made of injection mouldable polymer composites or nanocomposites for polycentric knee joint.

The present invention prosthetic knee joint adapter is made of rigid material which is clamped with top part and it is used to connect the socket with top part.

The present invention prosthetic knee joint's top and bottom part has tiny holes in the inclined axis for connecting the small and large links were also injection mouldable.

The present invention prosthetic knee joint's extension springs were fixed in the simply supported arrangement used for the extension bias.

The present invention prosthetic knee joint has tiny slot in the bottom and top part for connecting the small link is also made by injection moulding.

The slot for engaging and disengaging the knee mechanism, which is in the bottom part, is also a part of injection moulding.

The cylindrical rod for the locking mechanism of the knee joint with a tapping for connecting the holder for the engagement and disengagement is made of a rigid material.

The holder is having smooth curvature for easy handling of the lock.

The curves on the base of the bottom part along with bumper take care of the damping force.

The top/upper face of the bottom part takes care of the wear to avoid the buckling.

The top part is having contact with bottom part for braking.

The contact surfaces including stopper and wear between top and bottom of the prosthetic knee joint is made of polymer composites or nanocomposites.

The knee joint adapter was provided with two grooves as a stopper on its bottom face to avoid the rotation of the knee joint with respect to socket.

The top face of the top part of the knee joint has the provision of a slot for arresting the motion of the adapter.

In the present invention the additional machining time required to make the two tiny holes is reduced.

The present invention includes another way of holding the extension assist using the cylinder block, where the beam was extended in the overhanging or cantilever pattern to hold the extension spring.

Another way of fixing the extension bias makes the extension bias that it will not touch the bottom of the top part during the swing phase (flexion-extension stage).

The knee adapter is provided with the groove as a stopper to avoid the rotation of the knee joint with respect to socket, where the provision was given in the top face of the top part.

Those skilled in this technology can make various alterations and modifications without departing from the scope and spirit of the invention. Therefore, the scope of the invention shall be defined and protected by the following claims and their equivalents.

FIGS. 1-7 are merely representational and are not drawn to scale. Certain portions thereof may be exaggerated, while others may be minimized. FIGS. 1-7 illustrate various embodiments of the invention that can be understood and appropriately carried out by those of ordinary skill in the art.

In the foregoing detailed description of embodiments of the invention, various features are grouped together in a single embodiment for the purpose of streamlining the disclosure. This method of disclosure is not to be interpreted as reflecting an intention that the claimed embodiments of the invention require more features than are expressly recited in each claim. Rather, as the following claims reflect, inventive subject matter lies in less than all features of a single disclosed embodiment. Thus, the following claims are hereby incorporated into the detailed description of embodiments of the invention, with each claim standing on its own as a separate embodiment.

It is understood that the above description is intended to be illustrative, and not restrictive. It is intended to cover all alternatives, modifications and equivalents as may be included within the spirit and scope of the invention as defined in the appended claims. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein," respectively.

We claim:
1. A polymeric composite or nanocomposites based passive polycentric knee joint, the knee joint comprising:
   a top part having a top face and a bottom face, wherein the top face having an adapter coupled firmly with the top part to transfer the load from a stump of amputee via a socket;
   a bottom part having a top face and a bottom face;

at least one middle linkage pivotably coupling a middle posterior region of the top part with a middle posterior region of the bottom part;

two side linkages pivotably coupling sides of the top part with sides of the bottom part, a compression spring along with a cylindrical rod positioned in the interior of the bottom part which fully arrests flexion-extension motion of the knee joint when the top and bottom parts are engaged, and which allows for flexion-extension motion of the knee joint when the top and bottom parts are disengaged;

at least two extension springs coupling the top and bottom part through two tiny holes and through supporting beams in the top and bottom part for flexion and extension of the knee joint; and a bumper positioned in the base of the bottom part which contacts with a pylon to absorb the vibration and the terminal impact during the hip hike.

2. The knee joint as claimed in claim 1, wherein the two side linkages include a first side linkage and a second side linkage, wherein the first side linkage is disposed on a first side of the top part and on a first side of the bottom part, and wherein the second side linkage is disposed on a second side of the top part opposite the first side of the top part and on a second side of the bottom part opposite the first side of the bottom part.

3. The knee joint as claimed in claim 1, wherein the middle linkage pivotably couples an internal middle posterior region of the top part with an internal middle posterior region of the bottom part.

4. The knee joint as claimed in claim 1, wherein the bottom faces of the top part and the top face of the bottom part has two tiny holes which receive the extension springs through supporting beams which allows for the flexion and extension bias of the knee joint.

5. The knee joint as claimed in claim 1, wherein the bottom face of the top part and the top face of the bottom part are flat and comprise low friction surfaces.

6. The knee joint as claimed in claim 1, wherein the adapter of the top part is made up of rigid material which is clamped with the top part to connect the socket with the top part.

7. The knee joint as claimed in claim 1, wherein the bottom part further includes a holder in the top face which has a knurling surface for easy gripping to achieve a locking mechanism which fully arrests flexion-extension motion of the knee joint.

8. The knee joint as claimed in claim 1, wherein the cylindrical rod is connected by a threaded joint to a holder, said cylindrical rod and holder forming an integral part which functions to engage or disengage said top and bottom parts.

9. The knee joint as claimed in claim 1, wherein the cylindrical rod inactivates a four bar mechanism in order to fully arrest flexion-extension motion of the knee joint.

10. The knee joint as claimed in claim 1, wherein the cylindrical rod activates a four bar mechanism in order to allow flexion-extension motion of the knee joint.

11. The knee joint as claimed in claim 1, wherein the adapter is provided with a groove as a stopper in order to fully arrest rotation of the knee joint with respect to socket.

12. The knee joint as claimed in claim 1, wherein said supporting beam is an overhanging beam or a cantilever beam.

\* \* \* \* \*